United States Patent
Lee et al.

(10) Patent No.: US 10,028,901 B2
(45) Date of Patent: Jul. 24, 2018

(54) COSMETIC COMPOSITION FOR SKIN MOISTURIZING CONTAINING MINERALS AND QUINOA EXTRACT

(71) Applicant: Amorepacific Corporation, Seoul (KR)

(72) Inventors: Jin Young Lee, Yongin-si (KR); Sung Hoon Lee, Yongin-si (KR); Lee Kyoung Kwon, Yongin-si (KR); Byung Ryol Paik, Yongin-si (KR); Hae Kwang Lee, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 0 days.

(21) Appl. No.: 15/126,663

(22) PCT Filed: Mar. 26, 2015

(86) PCT No.: PCT/KR2015/002970
§ 371 (c)(1),
(2) Date: Sep. 16, 2016

(87) PCT Pub. No.: WO2015/147567
PCT Pub. Date: Oct. 1, 2015

(65) Prior Publication Data
US 2017/0087081 A1    Mar. 30, 2017

(30) Foreign Application Priority Data
Mar. 28, 2014 (KR) .......... 10-2014-0037143

(51) Int. Cl.
*A61K 8/97* (2017.01)
*A61Q 19/00* (2006.01)
(Continued)

(52) U.S. Cl.
CPC .......... *A61K 8/97* (2013.01); *A61K 8/19* (2013.01); *A61K 8/27* (2013.01); *A61K 8/64* (2013.01);
(Continued)

(58) Field of Classification Search
None
See application file for complete search history.

(56) References Cited

U.S. PATENT DOCUMENTS

2006/0280840 A1* 12/2006 Robertson ............... A23L 33/19
426/72
2012/0238506 A1* 9/2012 Msika .................... A23C 9/152
514/18.8
2013/0319449 A1 12/2013 Xavier et al.

FOREIGN PATENT DOCUMENTS

JP    2000-336024 A    12/2000
KR    10-0613422 B1    8/2006
(Continued)

OTHER PUBLICATIONS

Zalora ([retrieved from on-line website: https://www.zalora.com.my/laneige-laneige-cny-water-bank-set-2-white-1206623.html], last visit Feb. 2, 2017]).*

(Continued)

*Primary Examiner* — Ernst V Arnold
*Assistant Examiner* — Kyung S Chang
(74) *Attorney, Agent, or Firm* — Sughrue Mion, PLLC

(57) ABSTRACT

The present invention relates to a cosmetic composition for skin moisturization that contains minerals and a quinoa extract.

4 Claims, 2 Drawing Sheets

(51) Int. Cl.
    *A61K 8/64*           (2006.01)
    *A61K 8/19*           (2006.01)
    *A61K 8/27*           (2006.01)

(52) U.S. Cl.
    CPC ...... *A61Q 19/007* (2013.01); *A61K 2800/596* (2013.01); *A61K 2800/74* (2013.01)

(56) References Cited

FOREIGN PATENT DOCUMENTS

KR         10-0894628 B1     4/2009
KR    10-2011-0086137 A     7/2011

OTHER PUBLICATIONS

Amazon Q & A ([retreived from on-line website: https://www.amazon.com/Laneige-Water-Bank-Gel-Cream/dp/B004W3WDI8/ref=pd_sbs_194_1?_encoding=UTF8&psc=1&refRID=P3PS1T3T6PYSH5HJD1RX, last visit Feb. 2, 2017]).*
JP2000-336024A JPO Engligh Translation (2000).*
Quinoa ([retrieved from on-line website: https://authoritynutrition.com/foods/quinoa/, last visit Feb. 3, 2017)).*
Joseph S. Dublin, "The Universal Copyright Convention", California Law Review, pp. 1-32, 1954 (Year: 1954).*
International Searching Authority, International Search Report for PCT/KR2015/002970 dated Jun. 30, 2015 [PCT/ISA/210].
International Searching Authority, Written Opinion for PCT/KR2015/002970 dated Jun. 30, 2015 [PCT/ISA/237].

* cited by examiner

COSMETIC COMPOSITION FOR SKIN MOISTURIZING CONTAINING MINERALS AND QUINOA EXTRACT

CROSS REFERENCE TO RELATED APPLICATIONS

This application is a National Stage of International Application No. PCT/KR2015/002970 filed Mar. 26, 2015, claiming priority based on Korean Patent Application No. 10-2014-0037143 filed Mar. 28, 2014, the contents of all of which are incorporated herein by reference in their entirety.

TECHNICAL FIELD

The present invention relates to a cosmetic composition for skin moisturization containing minerals and a quinoa extract.

This application claims priority to Korea Patent Application No. 10-2014-0037143 filed on Mar. 28, 2014, and the contents are herein incorporated by reference.

BACKGROUND ART

The skin plays a vital role in protecting against the external environment, and such a function of the skin is called "barrier function". The skin barrier function is a protective function to protect against many different types of irritating stimuli from outside (e.g., chemicals, air pollutants, dryness, UV radiation, etc.) and to prevent excessive moisture loss through transcutaneous evaporation. Such a protective function can be maintained only when the stratum corneum consisting of keratinocytes is normally formed.

The outmost layer of the epidermis, stratum corneum (horny layer), is formed from keratinocytes and composed of layers of corneocytes that is the final outcome of keratinocyte maturation, and layers of lipids surrounding the corneocytes.

The corneocytes are characteristic cells derived from basal cells that continuously proliferate in the basal layer of the epidermis and undergo migration towards the skin surface whilst undergoing changes of shape and function. As a specified period of time elapses, old corneocytes are shedding from the skin surface and replaced by new ones. This process of repetitive modification is called the differentiation or keratinization of epidermal cells.

While forming the stratum corneum (horny layer) during the keratinization process, the keratinocytes also produce natural moisturizing factors (NMFs) and intercellular lipids (e.g., ceramides, cholesterols, fatty acids, etc.). This allows the stratum corneum to have solidity and plasticity and to serve a skin barrier function.

The stratum corneum is liable to lose its skin barrier function due to certain life habit factors like frequent soap washing of the skin on the face or whole body, environmental factors like dry air, air pollutants, etc., or endogenous diseases including atopic skin diseases, senile skin diseases, etc. With a growing number of factors related to this issue in modern times, the more people are suffering from the dry skin problem and the associated disturbances.

As well known in terms of the skin moisturization mechanism to maintain skin moisturization, it is very important to retain moisture in each layer of the skin by increasing the natural moisturizing factors (NMFs) that are made up of specific amino acids. The amino acids constituting the natural moisturizing factors (NMFs) are the breakdown product from the degradation of a protein called "filaggrin" that is produced by the epidermal keratinocytes. Hence, the ability to promote the production of filaggrin is of significance in the expression of the skin moisturizing function.

In addition, the keratinocytes express specific keratins at each stage of differentiation. For example, the keratinocytes in the basal layer primarily express keratin 5 (K5) and keratin 14 (K14). As the keratinocytes move towards the upper, visible layer from the basal layer, they express pairs of keratin 10 (K10) and keratin 1 (K1) in place of the K5 and K14 pairs. Loricrin, expressed late during terminal differentiation in epidermal keratinocytes, is linked to the cell membrane in the upper, granular layer to complete a protein, so it can be used as a marker for the terminal differentiation of keratinocytes.

Accordingly, there is a demand for development of a skin moisturizing preparation capable of promoting the expression of filaggrin and loricrin for forming the stratum corneum to promote the skin moisturization and strengthen the skin barrier for preventing moisture loss from the skin, in order to prevent skin ageing and maintain skin health against change of the external environment, including dry air, UV radiation and various air pollutants.

DISCLOSURE OF INVENTION

It is therefore an object of the present invention to provide a cosmetic composition that promotes the expression of filaggrin and loricrin for forming the stratum corneum in order to promote the skin moisturization and strengthen the skin barrier for preventing moisture loss from the skin.

The present invention is to provide a cosmetic composition for skin moisturization that contains minerals including at least one or more selected from the group consisting of calcium, manganese, magnesium, and zinc; and a quinoa extract.

When applied to the human body, the cosmetic composition for skin moisturization according to the present invention, containing a quinoa extract in addition to minerals, such as calcium, manganese, magnesium, or zinc, can promote the expression of natural moisturizing factors to enhance the skin moisturization and strengthen the skin barrier, thereby providing an excellent skin moisturizing effect to retain moisture in the skin.

BEST MODES FOR CARRYING OUT THE INVENTION

Figure 1:
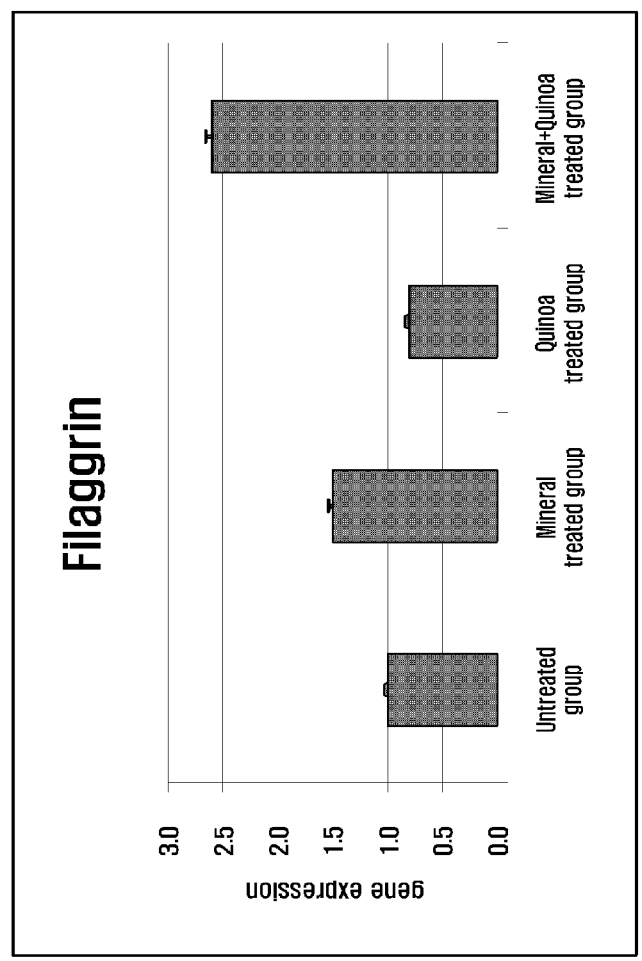
FIG. 1 is a graph showing the expression of filaggrin gene in a group treated with the composition of Comparative Example 1 (mineral treated group), a group treated with the composition of Comparative Example 2 (quinoa treated group), and a group treated with the composition of Example 1 (mineral+quinoa treated group) in relation to the untreated group.

The term "skin" as used herein refers to the tissue covering the surface of the body in animals. It may be used in a very inclusive sense to include scalp and hair in addition to the tissue covering the surface of the face or body.

The term "mineral(s)" as used herein refers to the element(s) except for oxygen (O), carbon (C), hydrogen (H), and nitrogen (N), as the major components of organic substances among the elements making up the human body and necessary to the physiological activities like the growth and maintenance of the human body.

The term "extract" as used herein may be used in a very inclusive sense to include all the substances obtained by extraction of natural components irrespective of the extraction method, the extracting solvent, the extracted component, or the form of the extracted substance.

The term "quinoa" as used herein refers to the flower, leaves, fruits, and seeds of a species Chenopodium quinoa of the goosefoot genus in the Amaranthaceae family and Chenopodium subfamily.

In one embodiment of the present invention, the quinoa extract may be prepared by a conventional method known to those skilled in the art, that is, an extraction method using a general solvent under normal temperature and pressure. Preferably, the quinoa extract is obtained by drying out quinoa flowers, leaves, fruits or seeds and then performing extraction with a solvent selected from the group consisting of water, anhydrous or hydrous lower C1-C4 alcohol, acetone, ethylacetate, butylacetate, and 1,3-butylene glycol, filtration and concentration.

In one embodiment of the present invention, the quinoa extract may be contained in an amount of 0.001 to 5 wt. % with respect to the total weight of the cosmetic composition for skin moisturization. The defined content of the quinoa extract, when applied to the skin in combination with the minerals, has an effect to enhance skin moisturization by promoting the filaggrin expression of the minerals and to strengthen the skin barrier by promoting the loricrin expression of the minerals. When the content of the quinoa extract is less than 0.001 wt. % with respect to the total weight of the cosmetic composition for skin moisturization, it is hard to make an effect of promoting the expression of filaggrin and loricrin. When the content of the quinoa extract is greater than 5 wt. %, there is the difficulty in the preparation in terms of stability and formulation.

In one embodiment of the present invention, the minerals may be contained in an amount of 0.001 to 1 wt. % with respect to the total weight of the cosmetic composition for skin moisturization. The defined content of the minerals, when applied to the skin in combination with the quinoa extract, has an effect to enhance skin moisturization by promoting the filaggrin expression of the minerals and to strengthen the skin barrier by promoting the loricrin expression of the minerals. When the content of the minerals is less than 0.001 wt. % with respect to the total weight of the cosmetic composition for skin moisturization, it is hard to make an effect of promoting the expression of filaggrin and loricrin. When the content of the minerals is greater than 1 wt. %, there is the difficulty in the preparation in terms of stability and formulation.

In one embodiment of the present invention, the minerals may be at least one or more selected from the group consisting of calcium, manganese, magnesium, and zinc.

In one embodiment of the present invention, the minerals may include all of calcium, manganese, magnesium, and zinc. The minerals including all of calcium, manganese, magnesium, and zinc is more effective to offer skin moisturization and strengthen the skin barrier than the minerals including one of calcium, manganese, magnesium, and zinc.

In one embodiment of the present invention, the minerals may include calcium, manganese, magnesium, and zinc at a weight ratio of 5 to 20:1 to 5:5 to 20:0.5 to 5.

In one embodiment of the present invention, the cosmetic composition for skin moisturization may have a function to promote keratinocyte differentiation. The minerals and the quinoa extract in the composition are excellent in promoting the gene expression of natural moisturizing factors and enhancing the differentiation of keratinocytes.

In one embodiment of the present invention, the cosmetic composition for skin moisturization may increase the natural moisturizing factors.

In one embodiment of the present invention, the natural moisturizing factors are filaggrin and loricrin.

In one embodiment of the present invention, the cosmetic composition for skin moisturization may be foods, cosmetics, or pharmaceutical preparations.

Hereinafter, the construction and effects of the present invention will be described in further detail with reference to the following examples and experimental examples, which are given only for the better understanding of the present invention and not construed to limit the scope of the present invention.

Example 1

0.2 kg of quinoa fruits and seeds are added to 1 L of a mixed solvent of water and ethanol (1:1 in v/v) for extraction, and the mixture is subjected to filtration with a membrane filter and then concentration to prepare a quinoa extract. 1 wt. % of the quinoa extract is added to 0.97 wt. % of minerals including magnesium sulfate, zinc sulfate, manganese sulfate, and calcium chloride dissolved in distilled water (to contain 0.35 wt. % of magnesium, 0.05 wt. % of zinc, 0.07 wt. % of manganese, and 0.5 wt. % of calcium). The resultant mixture is then subjected to a sterilizing filtration to prepare a composition.

Comparative Example 1

0.97 wt. % of minerals including magnesium sulfate, zinc sulfate, manganese sulfate, and calcium chloride is dissolved in distilled water (to contain 0.35 wt. % of magnesium, 0.05 wt. % of zinc, 0.07 wt. % of manganese, and 0.5 wt. % of calcium). The solution thus obtained is subjected to a sterilizing filtration to prepare a composition.

Comparative Example 2

In the same manner as described in Example 1, 0.2 kg of quinoa fruits and seeds are added to 1 L of a mixed solvent of water and ethanol (1:1 in v/v) for extraction. The mixture thus obtained is subjected to filtration with a membrane filter and then concentration to prepare a quinoa extract. 1 wt. % of the quinoa extract is added to distilled water, and the resultant mixture is then subjected to a sterilizing filtration to prepare a composition.

Experimental Example 1

Evaluation of NMF Promoting Function

The following experiment is performed to evaluate the composition of Example 1 according to the present invention in regards to the effect of promoting the expression of natural moisturizing factors.

Keratinocyte cells commercially available from Invitrogen Inc. are cultured in a keratinocyte growth medium (EpiLife) containing a human keratinocyte growth supplement (HKGS) for a defined period of time to obtain three-subculture cells. The three-subculture keratinocytes are cultured up to 70 to 80% on a 6-well plate. The individual wells are treated with the respective compositions and classified into an untreated group, a group treated with the composition of Comparative Example 1 (mineral treated group), a group treated with the composition of Comparative Example 2 (quinoa treated group), and a group treated with the composition of Example 1 (mineral+quinoa treated group). After two-day cultivation, the cultured keratinocyte cells are subjected to RNA extraction with TRIzol. Then cDNA synthesis is performed with a SuperScript reverse transcriptase III kit. As real-time PCR for comparing genes, 7500 Fast Real-Time PCR is carried out using a 2× TaqMan universal PCR mixture (10 μl), a 20X TaqMan expression assay mix (1 μl), cDNA (50 ng), and primers (Filaggrin: Hs00856927_g1*, Loricrin: Hs01894962_s1*).

The group treated with the composition of Comparative Example 1 (mineral treated group), the group treated with the composition of Comparative Example 2 (quinoa treated group), and the group treated with the composition of Example 1 (mineral+quinoa treated group) are analyzed in regards to the gene expression in comparison to the untreated group. The analysis results are charted in Table 1. The results concerning the expression of filaggrin and loricrin genes are presented in FIGS. 1 and 2, respectively.

TABLE 1

| Div. | Filaggrin gene expression (relative to control) | Loricrin gene expression (relative to control) |
|---|---|---|
| Control | 1.0 | 1.0 |
| Mineral treated group (Comparative Example 1) | 1.5 | 1.8 |
| Quinoa treated group (Comparative Example 2) | 0.8 | 1.1 |
| Mineral + quinoa treated group (Example 1) | 2.6 | 2.6 |

As can be seen from FIG. 1, the mineral+quinoa treated group treated with the composition of Example 1 according to the present invention is most excellent in the ability to promote the filaggrin gene expression for promoting the skin moisturization, whereas the quinoa treated group makes no effect in promoting the gene expression and the mineral treated group has an effect to promote the filaggrin gene expression.

Figure 2:
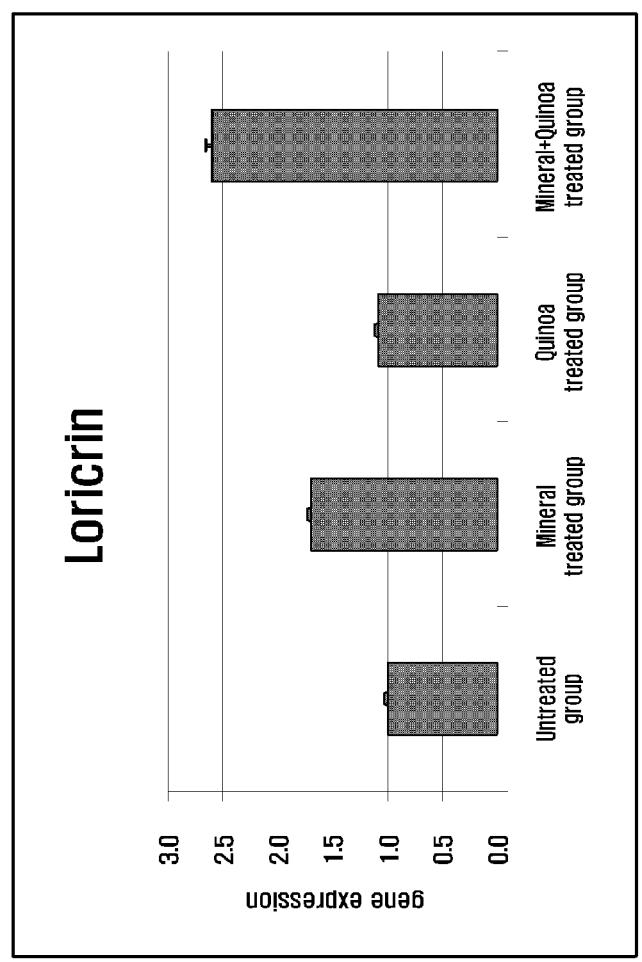
FIG. 2 is a graph showing the expression of loricrin gene in a group treated with the composition of Comparative Example 1 (mineral treated group), a group treated with the composition of Comparative Example 2 (quinoa treated group), and a group treated with the composition of Example 1 (mineral+quinoa treated group) in relation to the untreated group.

As shown in FIG. 2, the mineral+quinoa treated group treated with the composition of Example 1 according to the present invention is most excellent in the ability to promote the loricrin gene expression for strengthening the skin barrier, whereas the quinoa treated group makes no effect in promoting the gene expression and the mineral treated group has an effect to promote the loricrin gene expression.

This implicitly shows that the composition according to one embodiment of the present invention, containing both the minerals and the quinoa extract, has a synergistic effect to express the genes of natural moisturizing factors and carries out an excellent skin moisturizing function.

What is claimed is:

1. A cosmetic composition for skin moisturization comprising:
   minerals comprising all of calcium, manganese, magnesium, and zinc; and a quinoa extract,
   wherein a weight ratio of the calcium, manganese, magnesium, and zinc is 5 to 20:1 to 5:5 to 20:0.5 to 5, and
   wherein the cosmetic composition increases a natural moisturizing factor wherein the natural moisturizing factor comprises at least one or more selected from the group consisting of filaggrin and loricrin.

2. The cosmetic composition for skin moisturization as claimed in claim 1, wherein the quinoa extract is contained in an amount of 0.001 to 5 wt. % with respect to the total weight of the cosmetic composition for skin moisturization.

3. The cosmetic composition for skin moisturization as claimed in claim 1, wherein the minerals are contained in an amount of 0.001 to 1 wt. % with respect to the total weight of the cosmetic composition for skin moisturization.

4. The cosmetic composition for skin moisturization as claimed in claim 1, wherein the cosmetic composition for skin moisturization has a function to promote keratinocyte differentiation.

* * * * *